(12) United States Patent
Yu et al.

(10) Patent No.: US 9,095,431 B2
(45) Date of Patent: Aug. 4, 2015

(54) INVASIVE CARDIAC VALVE

(75) Inventors: Qifeng Yu, Shanghai (CN); Xiang Liu, Shanghai (CN); Yunlei Wang, Shanghai (CN); Chengyun Yue, Shanghai (CN); Qiyi Luo, Shanghai (CN)

(73) Assignee: SHANGHAI MICROPORT MEDICAL (GROUP) CO., LTD., Pudong New Area, Shanghai (CN)

( * ) Notice: Subject to any disclaimer, the term of this patent is extended or adjusted under 35 U.S.C. 154(b) by 5 days.

(21) Appl. No.: 13/519,930

(22) PCT Filed: Dec. 30, 2010

(86) PCT No.: PCT/CN2010/080497
§ 371 (c)(1), (2), (4) Date: Jul. 12, 2012

(87) PCT Pub. No.: WO2011/079803
PCT Pub. Date: Jul. 7, 2011

(65) Prior Publication Data
US 2012/0316642 A1 Dec. 13, 2012

(30) Foreign Application Priority Data

Dec. 30, 2009 (CN) .......................... 2009 1 0248065

(51) Int. Cl.
*A61F 2/06* (2013.01)
*A61F 2/24* (2006.01)
*A61F 2/30* (2006.01)

(52) U.S. Cl.
CPC .............. *A61F 2/2412* (2013.01); *A61F 2/2415* (2013.01); *A61F 2/2418* (2013.01); *A61F2002/3021* (2013.01); *A61F 2220/0075* (2013.01); *A61F 2230/008* (2013.01); *A61F 2230/0023* (2013.01); *A61F 2230/0054* (2013.01); *A61F 2230/0067* (2013.01)

(58) Field of Classification Search
CPC .................................................... A61F 2/2418
USPC ....................... 623/1.26, 2.17, 2.18
See application file for complete search history.

(56) References Cited

U.S. PATENT DOCUMENTS

| 7,914,569 B2 | 3/2011 | Nguyen et al. | |
|---|---|---|---|
| 2006/0265056 A1* | 11/2006 | Nguyen et al. | ............... 623/2.18 |
| 2009/0216312 A1 | 8/2009 | Straubinger et al. | |

FOREIGN PATENT DOCUMENTS

| CN | 2726561 | 9/2005 |
|---|---|---|
| CN | 1961845 | 5/2007 |

(Continued)

OTHER PUBLICATIONS

Gideon et al., Effects of design parameters on the radial force of percutaneous aortic valve stents, Apr. 2010, Cardiovascular Revascularization Medicine, vol. 11, pp. 101-104.*

(Continued)

*Primary Examiner* — Thomas J Sweet
*Assistant Examiner* — Brian Dukert
(74) *Attorney, Agent, or Firm* — Michael Best & Friedrich LLP

(57) ABSTRACT

An invasive cardiac valve comprises a tubular stent (1) and a valve (2). One end of the tubular stent (1) is of a frusto-conical structure, the other end is wide open, and the diameter of the open end is greater than the diameter of the frusto-conical end. The valve (2) is attached to the frusto-conical end of the tubular stent (1); and a delivery and retrieval hole (4) of the cardiac valve is provided at the top of the open end of the tubular stent (1). Because the diameter of the open end is greater than the diameter of the frusto-conical end, the cardiac valve can be effectively fixed in a position of aortic annulus to prevent the cardiac valve displacement caused by the impact of the blood flow. Because the valve (2) is attached to the frusto-conical end of the tubular stent (1), the valve (2) can totally avoid the left and right coronary ostia and does not affect the haemodynamics of the coronary artery. Because a delivery and retrieval hole (4) of the cardiac valve is provided at the top of the open end of the tubular stent (1), the cardiac valve can be retrieved and reset at any time by handle control if it is found to be placed in an improper position during the release process.

12 Claims, 8 Drawing Sheets

(56) References Cited

FOREIGN PATENT DOCUMENTS

| CN | 1961847 | 5/2007 |
| CN | 101243999 | 8/2008 |
| CN | 201168081 | 12/2008 |

OTHER PUBLICATIONS

PCT/CN2010/080497 International Search Report dated Apr. 7, 2011 (Translation and Original, 6 pages).

* cited by examiner

INVASIVE CARDIAC VALVE

CROSS-REFERENCE TO RELATED APPLICATIONS

This application is a national stage filing under 35 U.S.C. 371 of International Application No. PCT/CN2010/080497 filed Dec. 30, 2010, which claims foreign priority benefits to Chinese Patent Application No. 200910248065.7 filed Dec. 30, 2009. These applications are incorporated herein by reference in their entirety.

TECHNICAL FIELD

The present invention relates to the technical field of medical apparatus and instruments and, in particular, to an invasive cardiac valve.

BACKGROUND ART

The heart valve is composed of extremely thin and flexible lamellar tissue, and the valve is opened and closed along with the contraction and relaxation of the heart. The heart of a normal person beats about 100,000 times per day and the valve is opened and closed 100,000 times per day. Thus, the heart valve must remain flexible and tensile, and be able to bear the pressure of the heart and the washing of the blood over a long period of time during the lifespan of a person.

Cardiac valve disease is one of the most common heart diseases in China, and is mainly caused by valve damage from rheumatic fever. Coinciding with the aging population in recent years, valve degeneration (including calcification, myxoid degeneration and the like) and valve damage of metabolism disorder are increasing in China. In addition, congenital valve disease is also one of the most common types of congenital heart disease.

Fifty years have elapsed since Professor Albert START implanted the first artificial heart mechanical valve in the human body and Professor Alain CARPENTIER implanted the first artificial heart biological valve in the human body in the 1960s. Both of these valves and the research behind them have brought about a turning point of life for cardiac valve patients.

As for which is better, based on years of clinical application, we make such a comparison that the patient who has a mechanical heart valve implanted needs to take anticoagulant for the duration of his or her life. The anticoagulant has many adverse side effects, e.g., it is very likely to cause bleeding or thromboembolism. The biological valve, meanwhile, does not require taking anticoagulant. However, after the biological valve is implanted in the patient's body, the leaflet will undergo an early-mid-phase calcification, thereby resulting in valve stenosis or regurgitation. The calcification phenomenon is especially severe in the bodies of young and middle-aged patients.

For the above reason, in half a century after these two types of valves came into use, the scientists continued to explore new ways of improving and developing them. The early direction of research was mainly targeted at processing for preventing the calcification, and along with the development of the medical technology later, the research field is enlarged to the improvement of the valve structure.

Quite a lot of high risk cases related to cardiac valve diseases, e.g., patients suffering from severe valve regurgitation, aged patients not suitable for the surgical valve replacement operation, patients suffering from advanced tumor and valve regurgitation, and patients suffering from multiple organ dysfunction and valve diseases, need to be treated by a new invasive method with small trauma. Then, the invasive cardiac valve came under the motivation of the surgical cardiac valve replacement operation. In recent years, the percutaneous valve interventions, e.g., the percutaneous pulmonary valve stent replacement; the percutaneous aortic valve heart valve replacement; the percutaneous mitral valve repair and the percutaneous mitral valve encircling constriction, emerged as the times require; it has achieved success after the percutaneous valve interventions being successively applied to the human beings since 2000; the initial result shows that the methods are practicable; the validity and risk of the invasive treatment must be further evaluated and compared; and the invasive treatment is only applied to high risk patients who cannot tolerate the surgical operation. The valve implantation of the percutaneous intervention pulmonary valve; the percutaneous aortic valve heart valve replacement; the percutaneous mitral valve repair; the percutaneous mitral valve annuloplasty; and the percutaneous mitral valve encircling constriction are all practicable, and the representation is that the heart function is improved after the implantation.

The development of the invasive treatment within the past 10 years shows that all of the cases which can be treated by the medical department and the surgical department can be treated by intervention, and the cases which cannot be treated by surgical operations can also be treated by intervention. In this century, research related to invasive treatments for valve disease is accelerated; the percutaneous intervention cardiac valve implantation is developed from the experimental research stage to a research stage with a small scale clinical practice running parallel; and the intervention of the valve diseases may break the technical "bottleneck", rapidly achieve a wide clinical application, and again become the focus of attention in the field of interventional cardiology.

The U.S. Pat. No. 6,454,799 describes a balloon-expanded invasive cardiac valve, in which a biological valve is fixed on a plastically deformable stent; the valve is fixed to the balloon by radially compressing the stent; a percutaneous implantation is performed; and the stent is made to expand to be fixed by pressurizing the balloon after reaching the aortic valve. Such a balloon-expanded biological valve has the following disadvantages and problems: during the process of the compression of the stent and the expansion of the balloon, the tissue structure of the leaflet of the biological valve will suffer great damage, which severely affects the service life of the cardiac valve after the implantation; the stent of the cardiac valve is decided by the diameter of the balloon, if the selected size is too small, the valve has the risk of looseness or displacement, whereby a secondary balloon expansion is the only choice, and if the selected size is too large, there is a risk of tearing the aortic annulus, which results in the occurrence of other complications; with respect to such a cardiac valve, the balloon cannot be reset once it is expanded, and it will endanger the patient's life on the spot under the circumstance where the valve is placed in an improper position; and once the cardiac valve is implanted, if a problem arises, the valve cannot be retrieved and can be only replaced by means of a surgical operation.

The patent publication PCT/US2006/018514 describes a self-expanded invasive cardiac valve, in which a biological valve is fixed on a self-expanded stent; the stent is placed in a catheter of a carrier; a percutaneous implantation is performed; the stent is released after reaching the aortic valve; and the valve is made to be fixed with the aortic annulus by the structure of the stent itself. Such a self-expanded biological valve has the following disadvantages and problems: the stent is too long, and the design of the opening is unideal, which is likely to affect the hemodynamics of the left and right coronary ostia and results in disorder of the heart function; the cardiac valve which is released improperly cannot be reset, which will endanger the patient's life; and once the cardiac valve is implanted, if a problem arises, the valve cannot be retrieved and can be only replaced by means of a surgical operation.

The Chinese patent CN2726561 describes an invasive artificial cardiac valve, in which a leaflet is sutured on a tubular stent which is expandable and compressible; it is matched with a correspondingly designed implantation and retrieval device; a percutaneous implantation and an invasive extraction are performed; and a valve replacement is performed. Such a cardiac valve has the following disadvantages and problems: the stent is woven by threads, during the processes of compression and expansion, the grid is likely to be deformed, and the radial support force is unstable; there are a number of barbs at the outer side of the stent, although serving the purpose of preventing the displacement, they have a comparatively large damage to the vessel wall, meanwhile after the endothelialization, the retrieval of the stent is likely to tear the vessel, and the expected retrieval object is difficult to achieve; the design of the stent considers the positions of the left and right coronary ostia, but only two to three openings are left, the effect on the left and right coronary blood flows cannot be eliminated, and the positioning can hardly be performed when the cardiac valve is released.

It has been difficult to make much progress in the exploration of all the current products that have been clinically applied in the structure field. The current biological cardiac valve cannot be reset once it is opened, and it will endanger the patient's life on the spot under the circumstance where it is placed in an improper position.

SUMMARY OF THE INVENTION

In view of the above, the present invention provides an invasive cardiac valve to prevent the cardiac valve displacement caused by the impact of the blood flow and solve the problem that the cardiac valve cannot be reset once it is opened.

In order to achieve the above object, the present invention provides the following technical solution:

An invasive cardiac valve, comprises a tubular stent and a valve,
one end of the tubular stent is of a frusto-conical structure, the other end of the tubular stent is wide open, and the diameter of the open end is greater than the diameter of the frusto-conical end;
the valve is attached to the frusto-conical end of the tubular stent;
a delivery and retrieval hole of the cardiac valve is provided at the top of the open end of the tubular stent;
a frusto-cone generatrix of the frusto-conical end of the tubular stent is a straight line, a circular arc or a combination of a straight line and a circular arc.

Preferably, with respect to the above invasive cardiac valve, the open end of the tubular stent is of a horn shape, and the tubular stent is of a structure, in which both ends of the tubular stent are large and a middle part of the tubular stent is small, on the whole.

Preferably, with respect to the above invasive cardiac valve, the tubular stent is of a grid structure composed of a plurality of rhombic stent units.

Preferably, with respect to the above invasive cardiac valve, except the both ends, inside grids of the tubular stent are of a closed structure.

Preferably, with respect to the above invasive cardiac valve, the grids of the tubular stent gradually become smaller from the open end to the frusto-conical end.

Preferably, with respect to the above invasive cardiac valve, the grid at the opening is greater than diameters of left and right coronary arteries.

Preferably, with respect to the above invasive cardiac valve, the grid of the tubular stent is composed of stent rods, and the greater the grid is, the thicker the stent rod is.

Preferably, with respect to the above invasive cardiac valve, the open end of the tubular stent is composed of three rhombic grids which expand towards the surrounding in a petal shape, and there are three delivery and retrieval holes of the cardiac valve, which are provided at the top ends of the three rhombic grids respectively.

Preferably, with respect to the above invasive cardiac valve, the tubular stent is made of a nickel-titanium alloy material.

Preferably, with respect to the above invasive cardiac valve, the valve is fixed inside the tubular stent by means of sewing using a suture line.

Preferably, with respect to the above invasive cardiac valve, the valve is embodied as a leaflet and a skirt; and
the leaflet and the skirt are designed as an integral structure or a separated structure in which the leaflet is sewed on the skirt.

Preferably, with respect to the above invasive cardiac valve, the leaflet can be made of a biological tissue, a polymer material, a metallic material or a tissue engineered valve.

Preferably, with respect to the above invasive cardiac valve, the leaflet and the skirt adopt the separated structure, the skirt is sewed on the grid of the tubular stent, and the leaflet is sewed on the skirt or sewed on both the skirt and the grid of the stent.

Preferably, with respect to the above invasive cardiac valve, the skirt can be made of a biological tissue, a polymer material, a metallic material or a tissue engineered valve.

Preferably, with respect to the above invasive cardiac valve, the skirt is of a frusto-conical shape sewed by three skirt base bodies of a same trapezoidal shape.

Preferably, with respect to the above invasive cardiac valve, the base of the leaflet is of an arc structure, leaflet suture ears are provided at both ends of the base of the leaflet, the leaflet suture ears are sewed on the tubular stent, any two adjacent leaflet suture ears are sewed together by means of the suture line of one valve and another valve, and the leaflet and the skirt are sewed along the arc line of the base of the leaflet.

Preferably, with respect to the above invasive cardiac valve, the valve adopts an integral structure of the skirt and the leaflet, the valve is sewed on the grid of the tubular stent, and the middle part of the valve is sewed with a transverse arc line using a suture line.

Preferably, with respect to the above invasive cardiac valve, the valve can be made of a biological tissue, a polymer material, a metallic material or a tissue engineered valve.

Preferably, with respect to the above invasive cardiac valve, the valve is formed by three valve base bodies of the same shape;
at one end of the valve base body, both sides are provided with the leaflet suture ears, which are sewed on the tubular stent; roots of any two adjacent leaflet suture ears are sewed together; and
the transverse arc line sewed on the valve base body is sutured with the grid of the stent.

It can be seen from the above technical solutions that in the embodiments of the present invention, because the one end of the tubular stent is wide open, and the diameter of the open end is greater than the diameter of the frusto-conical end, the cardiac valve can be effectively fixed in a position of aortic annulus to prevent the cardiac valve displacement caused by the impact of the blood flow; because the valve is attached to the frusto-conical end of the tubular stent, the valve can totally avoid the left and right coronary ostia and does not affect the haemodynamics of the coronary artery; and because a delivery and retrieval hole of the cardiac valve is provided at the top of the open end of the tubular stent, the cardiac valve can be retrieved and reset at any time through a handle if it is found to be placed in an improper position during the release process.

In addition, the appearance design of the stent of the present invention accords with the human anatomical structure, and the stent can be effectively fixed in a position of aortic annulus to prevent the cardiac valve displacement caused by the impact of the blood flow.

Different designs of the width of the stent rod and different stent unit (grid) structures make the cardiac valve provide a uniform radial support force after being implanted to prevent the cardiac valve displacement caused by the impact of the blood flow.

Different designs of the width of the stent rod and different stent unit structures make the circumferential shape of the stent be deformable properly to be effectively attached to the portion of the aortic annulus.

The distinctive valve suture design can effectively prevent the risk of leakage of the surrounding of the vessel after the implantation of the cardiac valve.

The distinctive suture design of the joint position and joint point of the valve leaflet can effectively reduce the force effect produced on the stent during the running process of the valve and increase the durability of the stent.

The distinctive design of the shape of the biological valve leaflet increases the durability during the running process of the valve.

The size of the carrier matched with the present invention is comparatively small (18F), which can effectively reduce the stimulation and damage to the vessel; and the head end of the carrier can be bent through a handle, which accords with the biological makeup of the aortic arch to avoid the damage to the aortic arch portion.

BRIEF DESCRIPTION OF THE DRAWINGS

In order to describe the embodiments of the present invention or the technical solutions in the prior art more clearly, the figures to be used in the descriptions of the embodiments or the prior art will be briefly introduced below. It is obvious that the figures in the descriptions below are only some embodiments of the present invention, and those skilled in the art can also obtain other figures according to these figures without making inventive efforts.

DETAILED DESCRIPTION

The present invention discloses an invasive cardiac valve to prevent the cardiac valve displacement caused by the impact of the blood flow and solve the problem that the cardiac valve cannot be reset once it is opened.

The technical solutions in the embodiments of the present invention will be described clearly and completely below by taking the figures in the embodiments of the present invention into consideration, and it is obvious that the described embodiments are only parts of the embodiments of the present invention rather than all of the embodiments. Based on the embodiments in the present invention, all the other embodiments obtained by those skilled in the art without making inventive efforts are within the scope of protection of the present invention.

Embodiment 1

Figure 1:
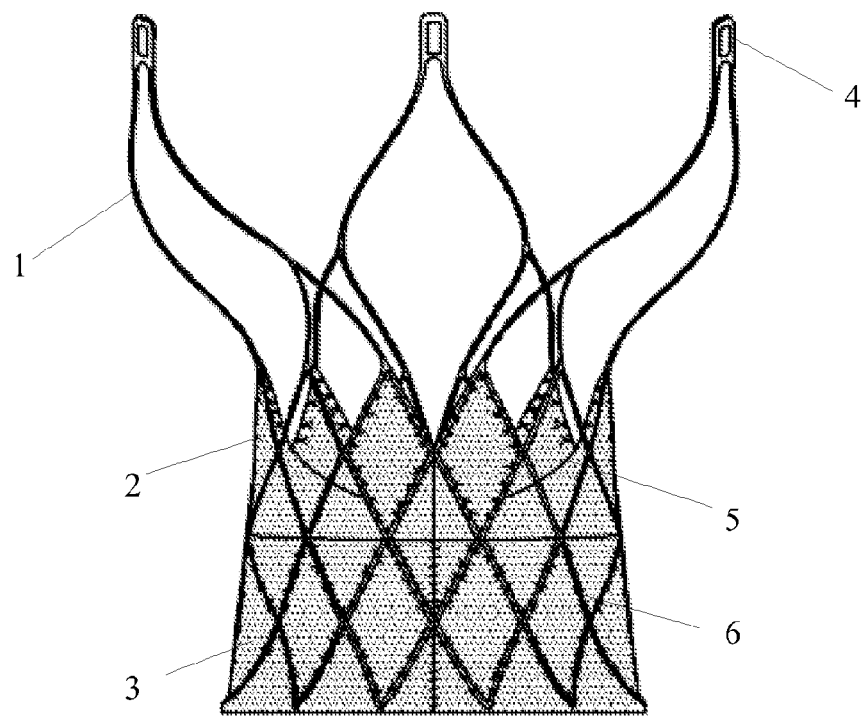
FIG. 1 is a front view of the cardiac valve provided by the Embodiment 1 of the present invention.
Figure 2:
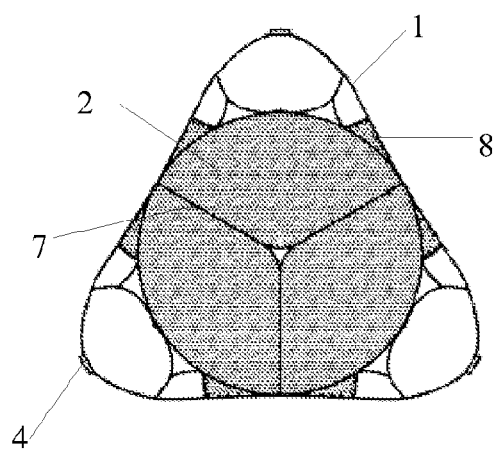
FIG. 2 is a top view of the cardiac valve provided by the Embodiment 1 of the present invention when the valve is in the closed state.
Figure 3:
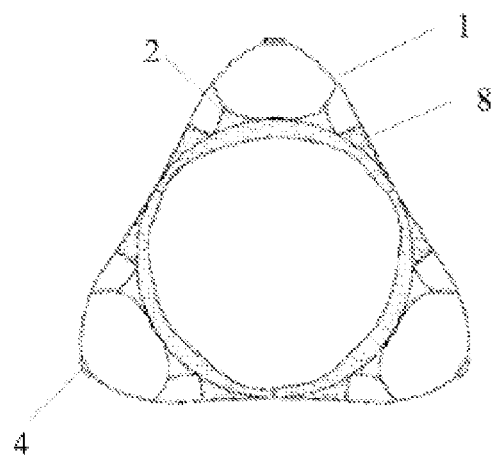
FIG. 3 is a top view of the cardiac valve provided by the Embodiment 1 of the present invention when the valve is in the open state.
Figure 4:
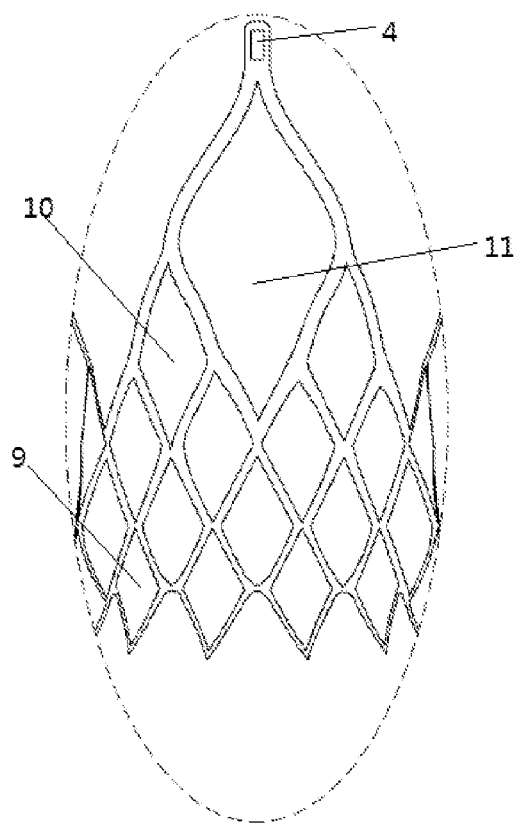
FIG. 4 is a partially enlarged view of the stent provided by the Embodiment 1 of the present invention.
Figure 5:
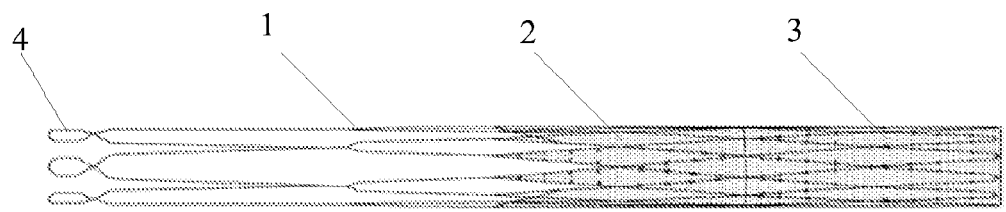
FIG. 5 is a schematic diagram of the compressed state of the cardiac valve provided by the Embodiment 1 of the present invention.

Please refer to FIGS. 1-5. FIG. 1 is a front view of the cardiac valve provided by the Embodiment 1 of the present invention, FIG. 2 is a top view of the cardiac valve provided by the Embodiment 1 of the present invention when the valve is in the closed state, FIG. 3 is a top view of the cardiac valve provided by the Embodiment 1 of the present invention when the valve is in the open state, FIG. 4 is a partially enlarged view of the stent provided by the Embodiment 1 of the present invention, and FIG. 5 is a schematic diagram of the compressed state of the cardiac valve provided by the Embodiment 1 of the present invention.

In these figures, 1 is the tubular stent, 2 is the leaflet, 3 is the skirt, 4 is the delivery and retrieval hole of the cardiac valve, 5 is the shape of the leaflet edge, 6 is the suture track of the skirt and the stent, 7 is the leaflet shut line, 8 is the suture of the leaflet and the stent, 9 is the first stent unit, 10 is the second stent unit, and 11 is the third stent unit.

The invasive cardiac valve provided by the present invention comprises a tubular stent 1, a leaflet 2 and a skirt 3.

One end of the tubular stent 1 is of a frusto-conical structure, the other end is wide open, and the diameter of the open end is greater than the diameter of the frusto-conical end; and a frusto-cone generatrix of the frusto-conical end of the tubular stent is a straight line, a circular arc or a combination of a straight line and a circular arc.

The leaflet 2 of the valve is sewed on the skirt 3, wherein the shape 5 of the leaflet edge is an arc, and the skirt 3 is sewed on and attached to one end of the frusto-conical structure of the tubular stent 1, wherein the reference sign 6 is the suture track of the skirt and the stent.

A delivery and retrieval hole 4 of the cardiac valve is provided on the top of the open end of the tubular stent 1.

The valve is of a closed circular shape in the closed state, and three leaflet shut lines 7 equally divide the entire circumference; and the valve is of a tubular shape in the open state.

In summary, in the embodiment of the present invention, because one end of the tubular stent is wide open, and the diameter of the open end is greater than the diameter of the frusto-conical end, the cardiac valve can be effectively fixed in a position of aortic annulus to prevent the cardiac valve displacement caused by the impact of the blood flow; because the valve is attached to the frusto-conical end of the tubular stent, the valve can totally avoid the left and right coronary ostia and does not affect the haemodynamics of the coronary artery; because the delivery and retrieval hole of the cardiac valve is provided on the top of the open end of the tubular stent, the cardiac valve can be retrieved and reset at any time through a handle if it is found to be placed in an improper position during the release process.

The open end of the tubular stent 1 is of a horn shape or a petal shape. The distinctive design of the opening of the stent and the connective mode with the delivery system enable the cardiac valve to be totally retrieved, reset or replaced with a new cardiac valve through a handle if it is found to be placed in an improper position or run abnormally after being totally released.

The tubular stent 1 is of a grid structure composed of a plurality of rhombic or other symmetrical patterns, each grid is called a stent unit, and the tubular stent 1 provided by the present invention is composed of a plurality of stent units. The grids of the tubular stent 1 gradually decrease from the open end to the frusto-conical end, i.e., the smaller the distance from the open end, the greater the stent unit is, and the stent unit at the open end of the horn is the largest. With respect to the first stent unit 9, the second stent unit 10 and the third stent unit 11 as shown in FIG. 4, the first stent unit 9 is a stent unit at the bottom of the tubular stent 1, the third stent unit 11 is a stent unit at the top of the open end of the horn, and the second stent unit 10 is a stent unit at the middle position of the tubular stent 1. It can be obviously seen from the figure that the grid of the third stent unit 11 is the largest, the grid of the first stent unit 9 is the smallest, and the size of the grid of the second stent unit 10 is between those of the first stent unit 9 and the third stent unit 11.

Those skilled in the art can understand that the present embodiment only lists three kinds of stent units, and the other stent units can adopt an increasing grid structure or a same grid structure as long as it is ensured that the grid structure at the open end is the largest and the grid structure at the straight tube end is the smallest, and the present invention is not only limited to the above three kinds of stent units.

The grid at the open end, i.e., the grid of the third stent unit 11, is greater than the diameters of the left and right coronary arteries to thereby avoid the left and right coronary arteries. The grid of the tubular stent is surrounded by the stent rods, i.e., each stent unit is a closed unit surrounded by the stent rods, and the greater the grid is, the thicker the stent rod is. Different designs of the width of the stent rod and different stent unit structures make the cardiac valve provide a uniform radial support force after being implanted to prevent the cardiac valve displacement caused by the impact of the blood flow, and can also make the circumferential shape of the stent be deformable properly to be effectively attached to the portion of the aortic annulus. Because the structure of the tubular stent is designed to be contracted layer by layer, the metal densities of the tubular stent from the top down are different and there are only three points at the opening of the horn. In order to provide a consistent support force, in the design, the higher the position is, the thicker the width of the stent rod is. It can be understood that the greater the grid is, the thicker the stent rod is, and the thinner the stent rod, it is more likely that the rod will be soft enough so that the cardiac valve is likely to be deformed at the lower part to be effectively attached to the portion of the aortic annulus, while at the upper part of the stent, the rod of cardiac valve stent would be hard enough to effectively prevent the cardiac valve displacement caused by the impact of the blood flow.

The open end of the tubular stent 1 is composed of three rhombic stent units which expand outwardly in a petal shape, and there are three delivery and retrieval holes 4 of the cardiac valve, which are provided at the top ends of the three rhombic stent units respectively. The tubular stent 1 is formed by laser etching a nickel-titanium alloy tube, and is heated treated, shaped, sand blasted, polished and finally come to such a designed structure.

Figure 6:
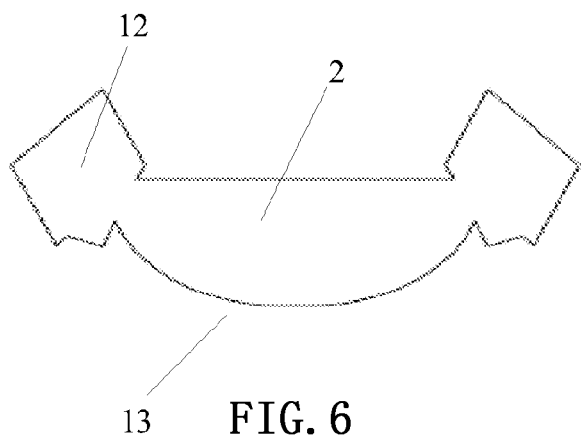
FIG. 6 is a schematic diagram of the design structure of the leaflet provided by the Embodiment 1 of the present invention.
Figure 7:
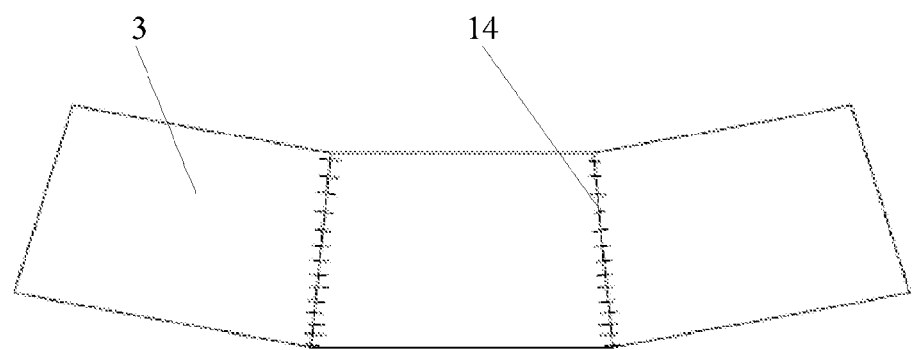
FIG. 7 is a schematic diagram of the structure of the skirt provided by the Embodiment 1 of the present invention.
Figure 8:
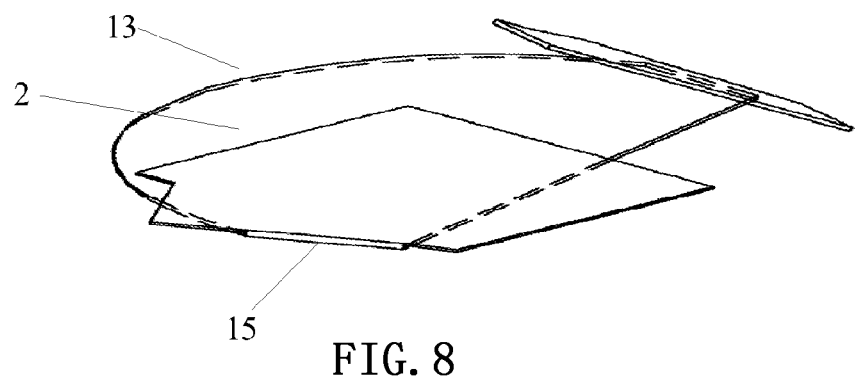
FIG. 8 is a folded view of the leaflet provided by the Embodiment 1 of the present invention.
Figure 9:
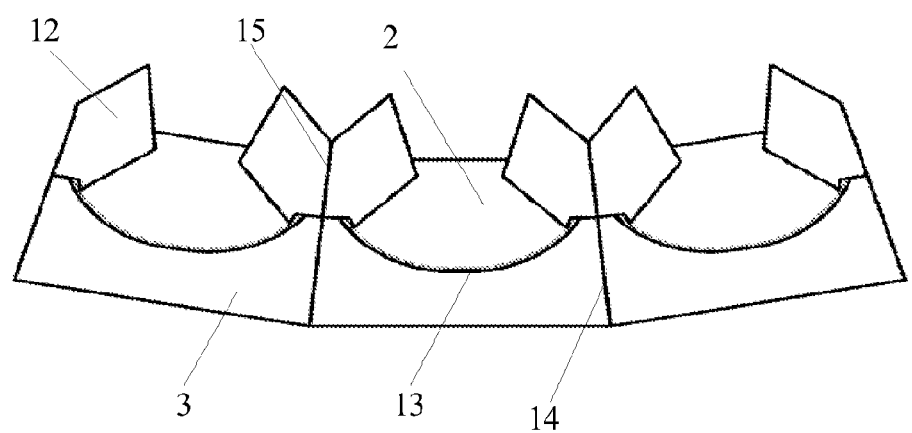
FIG. 9 is an unfolded view of the suture of the leaflet and the skirt provided by the Embodiment 1 of the present invention.
Figure 10:
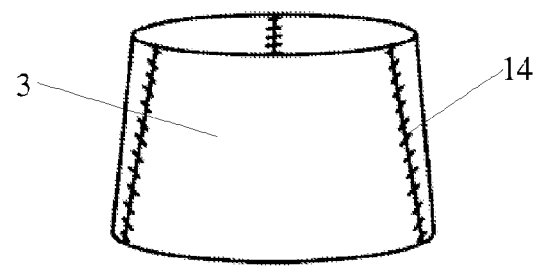
FIG. 10 is a perspective view of the suture of the skirt provided by the Embodiment 1 of the present invention.
Figure 11:
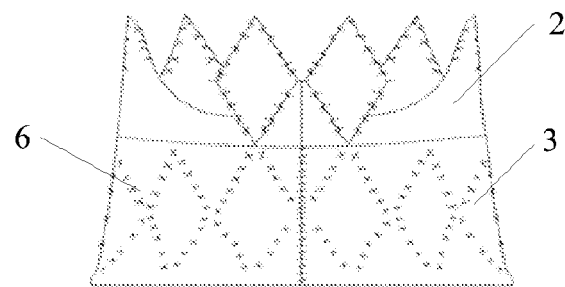
FIG. 11 is a schematic view of the suture track of the leaflet, the skirt and the stent provided by the Embodiment 1 of the present invention.

Please refer to FIGS. 6-11. FIG. 6 is a schematic diagram of the design structure of the leaflet provided by the Embodiment 1 of the present invention, FIG. 7 is a schematic diagram of the structure of the skirt provided by the Embodiment 1 of the present invention, FIG. 8 is a folded view of the leaflet provided by the Embodiment 1 of the present invention, FIG. 9 is an unfolded view of the suture of the leaflet and the skirt provided by the Embodiment 1 of the present invention, FIG. 10 is a perspective view of the suture of the skirt provided by the Embodiment 1 of the present invention, and FIG. 11 is a schematic view of the suture track of the leaflet, the skirt and the stent provided by the Embodiment 1 of the present invention;

In these figures, 2 is the leaflet, 3 is the skirt, 12 is the leaflet suture ear, 13 is the suture line of the leaflet and the skirt, 14 is the suture line of one skirt and another skirt, and 15 is the suture line of one valve and another valve.

The base of the leaflet 2 is of an arc structure, the leaflet suture ears 12 are provided at both ends (i.e., the both ends at which the arc line meets the straight line in the arc) of the base of the valve, the leaflet suture ears 12 are sewed on the tubular stent 1, any two adjacent leaflet suture ears 12 are sewed together by the position at which the leaflet suture ears 12 meet the base of the valve (i.e., the position of the suture line 15 of one valve and another valve), and the arc line at the bottom of the leaflet 2 is sewed on the skirt 3.

The leaflet 2 can be made of a biological tissue, e.g., bovine pericardium, porcine pericardium, porcine valve, caballine pericardium, bovine jugular vein, etc.; a polymer material, e.g., PU, e-PTFE, etc.; a metallic material, e.g., a nickel-titanium alloy sheet made by a special process; or a tissue engineered valve.

The skirt 3 is of a frusto-conical shape sewed by three skirt base bodies of a same trapezoidal shape. The adjacent edges of any two skirt base bodies are sewed together, and the reference sign 14 is the suture line of one skirt and another skirt. The skirt 3 can be made of a biological tissue, e.g., bovine pericardium, porcine pericardium, porcine valve, caballine pericardium, bovine jugular vein, etc.; a polymer material, e.g., PU, e-PTFE, etc.; a metallic material, e.g., a nickel-titanium alloy sheet made by a special process; or a tissue engineered valve.

The invasive cardiac valve provided by the present invention has multiple specifications, having diameters of 20~29 mm respectively, with influx diameter of 23~31 mm, and outfall diameter of 35~50 mm. The height of the cardiac valve is 35~50 mm.

Figure 12:
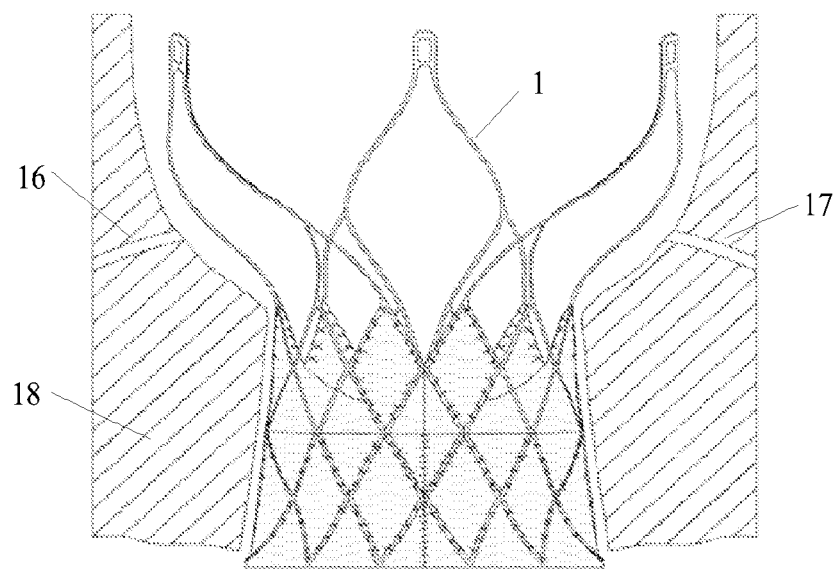
FIG. 12 is a schematic view of the positional relationship between the cardiac valve provided by the Embodiment 1 of the present invention and the coronary ostium after the cardiac valve is implanted.

Please refer to FIG. 12. FIG. 12 is a schematic view of the positional relationship between the cardiac valve provided by the Embodiment 1 of the present invention and the coronary ostium after the cardiac valve is implanted.

In the figure, 1 is the tubular stent, 16 is the left coronary artery, 17 is the right coronary artery, and 18 is the aortic annulus.

The cardiac valve is placed in the position of the aortic annulus 18. Because the head, i.e., the opening of the horn, of the cardiac valve provided by the present invention is not provided with a valve, and the grid (i.e., stent unit) is comparatively large, the grid is much larger than the left and right coronary arteries 16, 17 to thereby avoid the left and right coronary arteries 16, 17.

Embodiment 2

Figure 13:
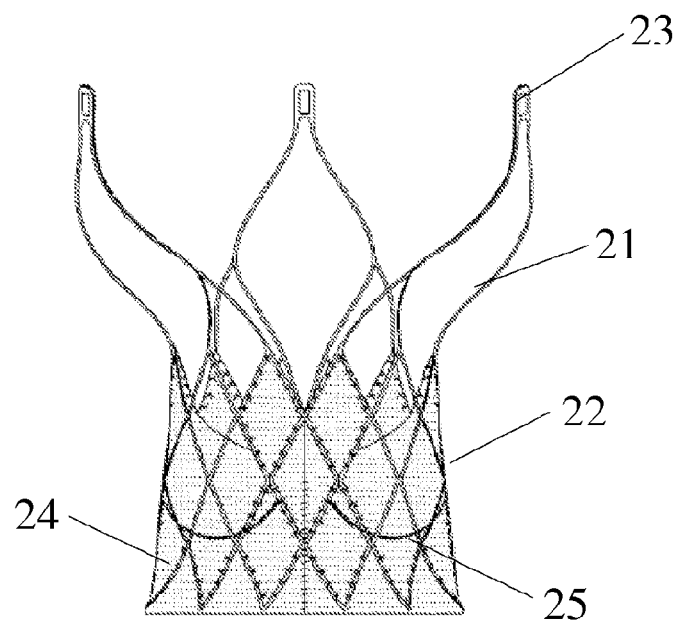
FIG. 13 is a front view of the cardiac valve provided by the Embodiment 2 of the present invention.
Figure 14:
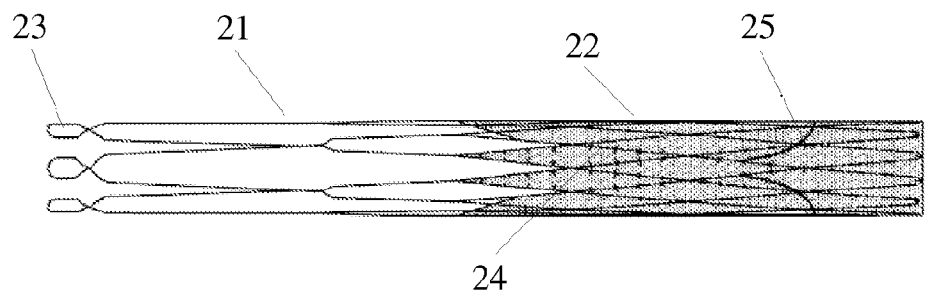
FIG. 14 is a schematic diagram of the compressed state of the cardiac valve provided by the Embodiment 2 of the present invention.
Figure 15:
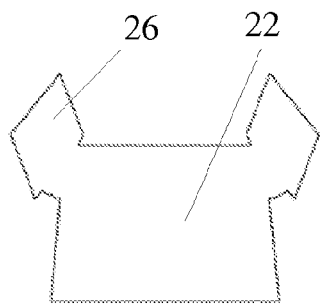
FIG. 15 is a schematic diagram of the design structure of the valve provided by the Embodiment 2 of the present invention.
Figure 16:
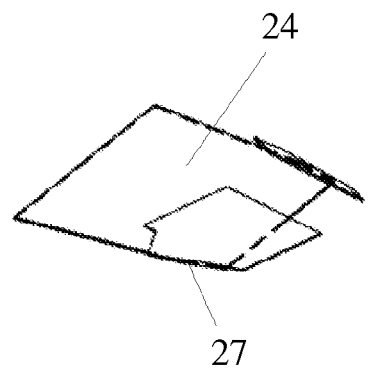
FIG. 16 is a folded view of the valve provided by the Embodiment 2 of the present invention.
Figure 17:
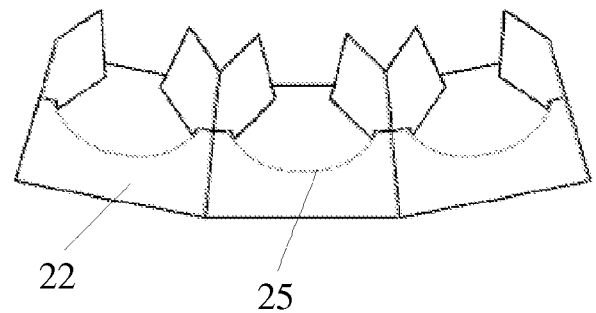
FIG. 17 is an unfolded view of the suture of the valve provided by the Embodiment 2 of the present invention.
Figure 18:
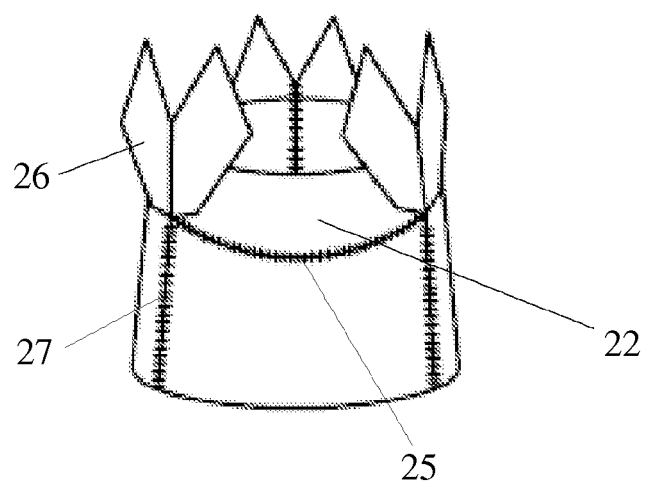
FIG. 18 is a perspective view of the suture of the valve provided by the Embodiment 2 of the present invention.
Figure 19:
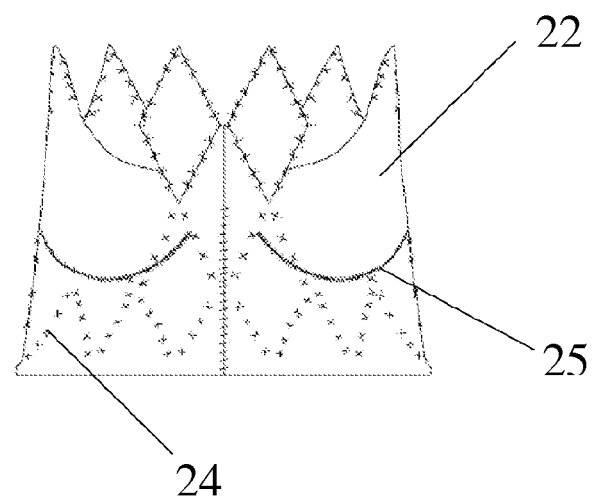
FIG. 19 is a schematic view of the suture track of the valve and the stent provided by the Embodiment 2 of the present invention.
Figure 20:
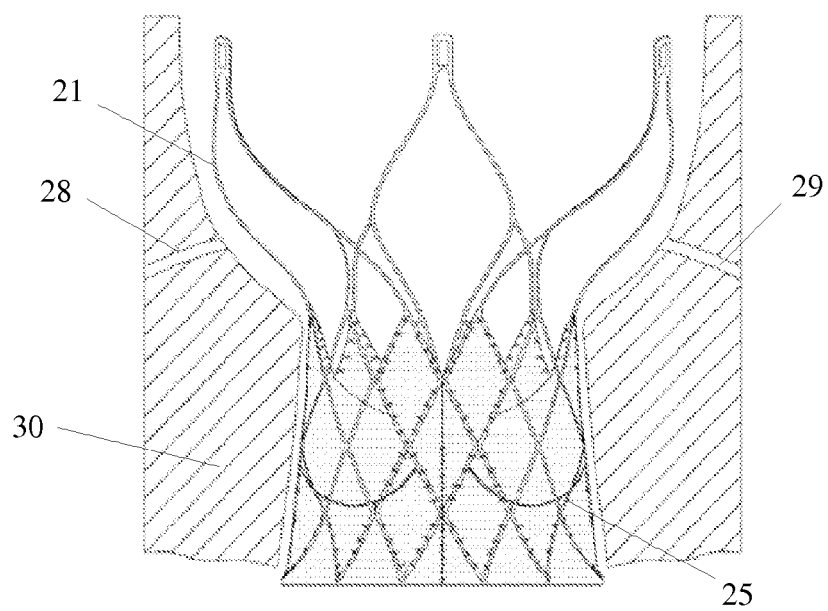
FIG. 20 is a schematic view of the positional relationship between the cardiac valve provided by the Embodiment 2 of the present invention and the coronary ostium after the cardiac valve is implanted.

Please refer to FIGS. 13-20. FIG. 13 is a front view of the cardiac valve provided by the Embodiment 2 of the present invention, FIG. 14 is a schematic diagram of the compressed state of the cardiac valve provided by the Embodiment 2 of the present invention, FIG. 15 is a schematic diagram of the design structure of the valve provided by the Embodiment 2 of the present invention, FIG. 16 is a folded view of the valve provided by the Embodiment 2 of the present invention, FIG. 17 is an unfolded view of the suture of the valve provided by the Embodiment 2 of the present invention, FIG. 18 is a perspective view of the suture of the valve provided by the Embodiment 2 of the present invention, FIG. 19 is a schematic view of the suture track of the valve and the stent provided by the Embodiment 2 of the present invention, and FIG. 20 is a schematic view of the positional relationship between the cardiac valve provided by the Embodiment 2 of the present invention and the coronary ostium after the cardiac valve is implanted.

In these figures, 21 is the tubular stent, 22 is the valve, 23 is the delivery and retrieval hole of the cardiac valve, 24 is the suture of the valve and the stent, 25 is the suture track of the stent and the valve, 26 is the leaflet suture ear, 27 is the suture line of one valve and another valve, 28 is the left coronary artery, 29 is the right coronary artery, and 30 is the aortic annulus.

The structure of the tubular stent 21 is the same as that in the Embodiment 1. The delivery and retrieval hole 23 of the cardiac valve is also provided at the open end, and no unnecessary details are further given here.

The valve 22 is sewed into a shape by three valve base bodies of the same irregular shape, and the general shape is the same as the shape of the valve sewed by the leaflet and the skirt. In this valve 22, the leaflet and the skirt are designed as an integral structure.

At one end of the valve base body, both sides are provided with the leaflet suture ears 26 sewed on the tubular stent 21.

In the valve base body of the valve 22, the middle part of the valve is sewed with a transverse arc line using a suture line. The transverse suture line of the valve is sewed with and fixed to the tubular stent 21, and the suture track 25 of the stent and the valve is just the transverse arc line.

Any two adjacent leaflet suture ears 26 are mutually sewed together, and the suture line 27 of one valve and another valve is just the suture position.

The aortic valve of the present invention can be placed in the position of the aortic valve in the following manners:

Implementation Method 1:

Surgical operation, thoracotomy replacement: after the host aortic valve is expanded, the cardiac valve is placed in the position of the aortic valve.

Implementation Method 2:

The cardiac valve is placed in the carrier; a small incision is cut at the chest; a sheathing canal with the inner diameter greater than that of the carrier penetrates at the position at the tip of the heart; guided by a DSA device, a balloon is placed in the aortic valve; the balloon expands the valve where a lesion occurs after being pressurized; after the balloon is withdrawn, the carrier mounted with the cardiac valve is placed in through the sheathing canal; guided by the DSA, the cardiac valve is released after reaching the position of the host aortic valve; and meanwhile the carrier is withdrawn to the outside of the body and the incision is sutured.

Implementation Method 3:

A small opening is cut at the femoral artery for the placement of the sheathing canal; guided by the DSA device, a balloon is placed in the host aortic valve; the balloon expands the valve where a lesion occurs after being pressurized; after the balloon is withdrawn, the carrier mounted with the cardiac valve is placed in through the sheathing canal; and guided by the DSA, the cardiac valve is released after reaching the position of the host aortic valve. The cardiac valve can be retrieved through the carrier if it is found to be placed in an improper position during the release process. After the valve is totally opened and before the valve breaks away from the carrier, it is permissible to firstly detect whether the cardiac valve is placed in a proper position and whether the valve runs normally; and if the selected aortic valve is found to have an improper size or an unideal running status, the cardiac valve can be totally retrieved through the carrier, withdrawn to the outside of body and replaced with a new cardiac valve.

In summary, because one end of the tubular stent is wide open and the diameter of the open end is greater than the diameter of the frusto-conical end, the present invention can be effectively fixed in a position of aortic annulus to prevent the cardiac valve displacement caused by the impact of the blood flow; because the valve is attached to the frusto-conical end of the tubular stent, the present invention can totally avoid the left and right coronary ostia and does not affect the haemodynamics of the coronary artery; and because a delivery and retrieval hole of the cardiac valve is provided on the top of the open end of the tubular stent, the cardiac valve can be retrieved and reset at any time through a handle if it is found to be placed in an improper position during the release process. The present invention can adopt an integral design of the leaflet and the skirt or a separated design of the two where the setting is performed by suturing.

In addition, the appearance design of the stent of the present invention accords with the human anatomical structure, and the stent can be effectively fixed in a position of aortic annulus, to prevent the cardiac valve displacement caused by the impact of the blood flow.

Different designs of the width of the stent rod and different stent unit (grid) structures make the cardiac valve provide a uniform radial support force after being implanted, to prevent the cardiac valve displacement caused by the impact of the blood flow.

Different designs of the width of the stent rod and different stent unit structures make the circumferential shape of the stent be deformable properly to be effectively attached to the portion of the aortic annulus.

The distinctive valve suture design can effectively prevent the risk of leakage of the surrounding of the vessel after the implantation of the cardiac valve.

The distinctive suture design of the joint position and joint point of the valve leaflet can effectively reduce the force effect produced on the stent during the running process of the valve and increase the durability of the stent.

The distinctive design of the shape of the biological valve leaflet increases the durability during the running process of the valve.

The size of the carrier matched with the present invention is comparatively small (18F), which can effectively reduce the stimulation and damage to the vessel; and the head end of the carrier can be bent through a handle, which accords with the biological makeup of the aortic arch to avoid the damage to the aortic arch portion.

The respective embodiments in the Description are described in a progressive manner, each embodiment stresses differences from the other embodiments, and the respective embodiments can refer to each another with respect to their same or similar parts.

The above descriptions of the disclosed embodiments enable those skilled in the art to achieve or use the present invention. Multiple amendments to these embodiments are obvious to those skilled in the art, and general principles defined in this text can be carried out in the other embodiments in case of not breaking away from the spirit and scope of the present invention. Thus, the present invention will not be limited to these embodiments shown in this text, but shall accord with the widest scope consistent with the principles and novel characteristics disclosed by this text.

The invention claimed is:

1. An invasive cardiac valve having a top end and a bottom end, comprising a tubular stent and a valve, characterized in that a first portion of the tubular stent is of a frusto-conical structure and defines a first end, a second portion of the tubular stent defines a wide open second end, the second portion of the tubular stent includes three rhombic grids which expand towards the second end in a petal shape, and the diameter of the second end is greater than the diameter of the first end, wherein the three rhombic grids of the tubular stent are composed of stent rods, and the thickness of the stent rods gradually decreases from the second end to the first end;

the valve is attached to the first end of the tubular stent;

a delivery and retrieval hole of the cardiac valve is provided at the second end of the tubular stent, wherein there are three delivery and retrieval holes of the cardiac valve, which are provided at the second end of the three rhombic grids respectively;

a frusto-cone generatrix of the first end of the tubular stent is a straight line, a circular arc or a combination of a straight line and a circular arc;

the cardiac valve defines at least two stent units, the at least two stent units gradually becoming smaller from the top end to the bottom end;

the valve is embodied as a leaflet and a skirt, and the leaflet and the skirt are designed as an integral structure;

the valve is sewed on the grids of the tubular stent, and a middle part of the valve is sewed with a transverse arc line using a suture line; and the transverse arc line is sutured with the grids of the stent.

2. The invasive cardiac valve according to claim 1, characterized in that the tubular stent is of a grid structure composed of a plurality of rhombic stent units.

3. The invasive cardiac valve according to claim 1, characterized in that the portions of the rhombic grids positioned at the second end and at a location spaced from the second end are of an open structure, and the portion of the rhombic grids of the tubular stent between the second end and the location spaced from the second end are of a closed structure.

4. The invasive cardiac valve according to claim 1, characterized in that each of the three rhombic grids at the second end has a size that is greater than the diameter of the left and right coronary arteries.

5. The invasive cardiac valve according to claim 1, characterized in that the tubular stent is made of a nickel-titanium alloy material.

6. The invasive cardiac valve according to claim 1, characterized in that the valve is fixed inside the tubular stent by means of sewing using a suture line.

7. The invasive cardiac valve according to claim 1, characterized in that the leaflet and the skirt can be made of a biological tissue, a polymer material, a metallic material or a tissue engineered valve.

8. The invasive cardiac valve according to claim 1, characterized in that the skirt is of a frusto-conical shape sewed by three skirt base bodies of a same trapezoidal shape.

9. The invasive cardiac valve according to claim 1, characterized in that the valve can be made of a biological tissue, a polymer material, a metallic material or a tissue engineered valve.

10. The invasive cardiac valve according to claim 1, characterized in that the valve is formed by three valve base bodies of the same shape;

at one end of the valve base body, both sides are provided with leaflet suture ears, which are sewed on the tubular stent;

roots of any two adjacent leaflet suture ears are sewed together.

11. The invasive cardiac valve according to claim 1, characterized in that the tubular stent further includes a plurality of grids including the three rhombic grids.

12. The invasive cardiac valve according to claim 1, characterized in that the cardiac valve further includes a plurality of grids including the three rhombic grids.

* * * * *